(12) United States Patent
Derouet et al.

(10) Patent No.: US 9,629,674 B2
(45) Date of Patent: Apr. 25, 2017

(54) ASSEMBLY INCLUDING AT LEAST ONE IMPLANT AND A GRIPPING DEVICE, AND METHOD FOR PREPARING FOR FITTING THE IMPLANT OF AN ASSEMBLY OF THE AFOREMENTIONED TYPE

(71) Applicant: NEOSTEO, Nantes (FR)

(72) Inventors: Guillaume Derouet, La Turballe (FR); Maxime Dechelette, Petit Mars (FR)

(73) Assignee: NEOSTEO, Nantes (FR)

( * ) Notice: Subject to any disclaimer, the term of this patent is extended or adjusted under 35 U.S.C. 154(b) by 0 days.

(21) Appl. No.: 14/758,398

(22) PCT Filed: Dec. 20, 2013

(86) PCT No.: PCT/FR2013/053209
§ 371 (c)(1),
(2) Date: Jun. 29, 2015

(87) PCT Pub. No.: WO2014/102490
PCT Pub. Date: Jul. 3, 2014

(65) Prior Publication Data
US 2015/0351846 A1      Dec. 10, 2015

(30) Foreign Application Priority Data

Dec. 31, 2012  (FR) ...................... 12 62987
Dec. 31, 2012  (FR) ...................... 12 62988

(51) Int. Cl.
*A61B 17/06*   (2006.01)
*A61B 19/02*   (2006.01)
(Continued)

(52) U.S. Cl.
CPC ............ *A61B 17/865* (2013.01); *A61B 50/20* (2016.02); *A61B 50/30* (2016.02); *A61B 90/90* (2016.02); *A61B 90/94* (2016.02)

(58) Field of Classification Search
CPC ....... A61B 17/865; A61B 50/20; A61B 50/30; A61B 90/90; A61B 90/94; A61B 19/026; A61F 2/0095
(Continued)

(56) References Cited

U.S. PATENT DOCUMENTS 6,802,421 B1    10/2004  Impellizzeri
2007/0095689 A1*  5/2007  Pratt .................. A61B 50/30
                                                    206/366
(Continued)

FOREIGN PATENT DOCUMENTS

DE    10 74 819 B      2/1960
EP    1 241 998 B1    11/2004
(Continued)

OTHER PUBLICATIONS

International Search Report, dated Mar. 20, 2014, from corresponding PCT application.

*Primary Examiner* — Jacob K Ackun
*Assistant Examiner* — Rafael Ortiz
(74) *Attorney, Agent, or Firm* — IPSILON USA, LLP

(57) ABSTRACT

A kit includes: an implant having a distal end for inserting the implant into the body; and a gripper in the form of a hollow elongate body that is open at at least one end, that is slotted longitudinally, and made, at least partly, of an elastically-deformable material, the slot opening out into the axial cavity of the body, inside which the implant is suitable for insertion, with its distal end projecting from the "distal" end of the body. The kit includes at least one reception sheath for receiving the distal end of the implant in order to separate the implant from its gripper by moving the sheath and the gripper relative to each other in the direction that breaks the alignment between them, the sheath has a bearing (Continued)

seat against which the implant bears both when the implant is inserted in the sheath, and when separated from its gripper.

9 Claims, 6 Drawing Sheets

(51) Int. Cl.
    *A61L 15/00*     (2006.01)
    *A61B 17/86*     (2006.01)
    *A61B 50/20*     (2016.01)
    *A61B 50/30*     (2016.01)
    *A61B 90/90*     (2016.01)
    *A61B 90/94*     (2016.01)

(58) Field of Classification Search
    USPC ....... 206/438, 223, 570, 571, 572, 338, 339, 206/363, 63.3, 63.5, 564, 368–370, 804, 206/577
    See application file for complete search history.

(56) References Cited

U.S. PATENT DOCUMENTS

| | | | |
|---|---|---|---|
| 2008/0230423 A1* | 9/2008 | Loeffler | A61B 17/865 206/438 |
| 2011/0238071 A1* | 9/2011 | Fernandez-Scoma | A61C 1/084 606/80 |
| 2011/0288596 A1* | 11/2011 | Brand | A61B 50/30 606/290 |
| 2011/0297571 A1 | 12/2011 | Brand | |
| 2012/0181202 A1* | 7/2012 | Guenter | A61C 8/0087 206/438 |
| 2013/0000262 A1* | 1/2013 | Richart | A61B 17/865 53/492 |

FOREIGN PATENT DOCUMENTS

| | | |
|---|---|---|
| EP | 2 392 286 A1 | 12/2011 |
| FR | 2 959 216 A1 | 10/2011 |
| WO | 2009/024189 A2 | 2/2009 |

\* cited by examiner

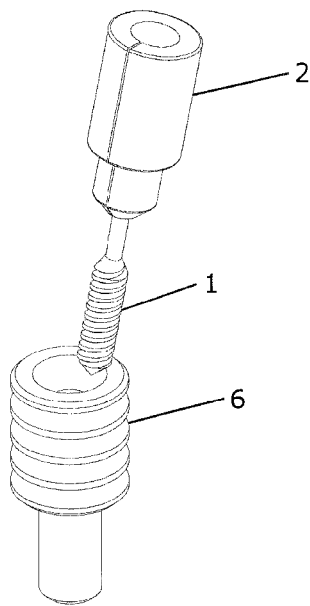 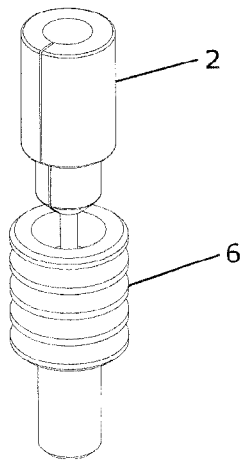 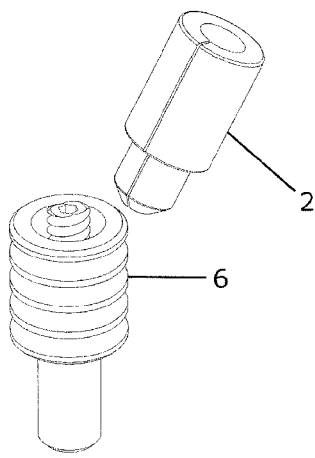
FIG 8   FIG 9   FIG 10
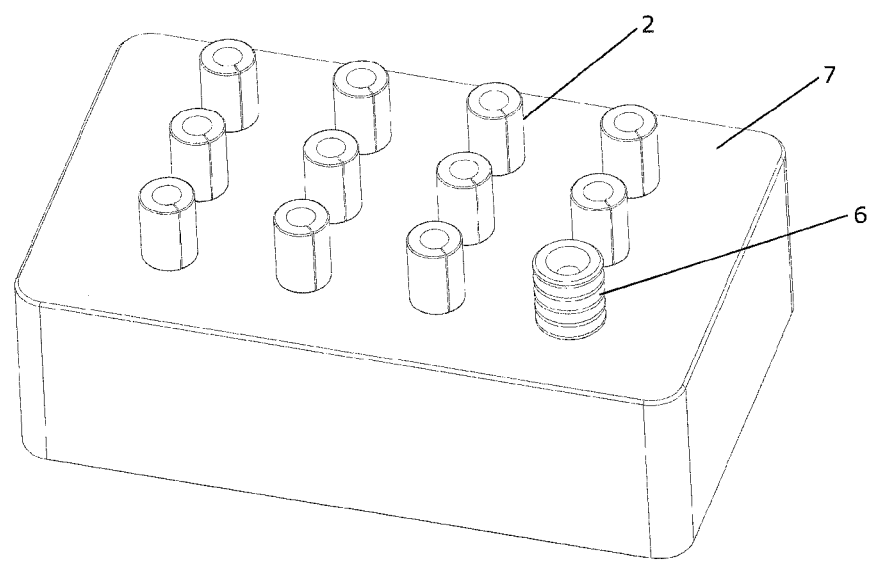
FIG 11

ASSEMBLY INCLUDING AT LEAST ONE IMPLANT AND A GRIPPING DEVICE, AND METHOD FOR PREPARING FOR FITTING THE IMPLANT OF AN ASSEMBLY OF THE AFOREMENTIONED TYPE

The present invention relates to a kit comprising at least an implant and a gripper, and to a method of preparing to implant the implant of a kit of the above-mentioned type.

It relates more particularly to a kit of the type comprising:
- an implant that presents a distal end for inserting the implant into the human or animal body, and a proximal end, also referred to as the head of the implant, that is preferably suitable for co-operating with a handling tool; and
- a gripper for gripping said implant, the gripper being in the form of a hollow elongate body that is open at at least one end, and preferably at each of its ends, and that is slotted longitudinally along at least a portion of its length, and preferably along its entire length, the body being made, at least in part, of an elastically-deformable material that tends to return the edges of the slot towards each other, the slot of said body opening out into the axial cavity of said body, inside which the implant is suitable for being inserted, with its distal end projecting from the "distal" end of said body.

Such kits are known in the prior art, as shown in particular in patent EP 1 241 998.

Hygiene standards require protocols to be put into place that enable implants to be implanted without the surgeon's hand touching the implant.

Unfortunately, grippers that have been developed in the past, pose a problem in particular when coupling the implant, such as a screw, with a handling tool, such as a screwdriver, that is suitable for enabling the implant to be turned so as to insert it in a part, such as a bone, of the human or animal body.

Specifically, grippers such as those described in patent EP 1 241 998 are made of an elastically-deformable material, such as rubber, that imparts flexibility to the gripper. Such flexibility makes the gripper easier to deform in the direction that causes the edges of the slot to move apart, so as to enable the implant to be removed from the gripper. Without such flexibility, such deformation is impossible.

However, such flexibility, which is advantageous in making it easier to separate the implant from the gripper, becomes a drawback while coupling the implant with a handling tool. Specifically, the handling tool exerts axial thrust on the head of the implant so as to couple it with the implant. Under the effect of the axial thrust, the implant tends to slide inside the gripper in such a manner that there is a risk of the implant escaping from the gripper, without being coupled to the handling tool. It is then necessary to touch the implant directly, which is not recommended. Furthermore, when the implant escapes from the gripper, there exists a risk of it landing on a surface that is not sterile.

An object of the present invention is thus to propose a kit of the above-mentioned type having a design that makes it easier to couple the implant with a handling tool without touching the implant.

To this end, the invention provides a kit comprising at least:
- an implant that presents a distal end for inserting the implant into the human or animal body, and a proximal end, also referred to as the head of the implant, that is preferably suitable for co-operating with a handling tool; and
- a gripper for gripping said implant, the gripper being in the form of a hollow elongate body that is open at at least one end, and preferably at each of its ends, and that is slotted longitudinally along at least a portion of its length, and preferably along its entire length, the body being made, at least in part, of an elastically-deformable material that tends to return the edges of the slot towards each other, the slot of said body opening out into the axial cavity of said body, inside which the implant is suitable for being inserted, with its distal end projecting from the "distal" end of said body;

said kit being characterized in that it further comprises means for assisting in separating the gripper from the implant without touching the implant, the means comprising at least one reception sheath for receiving the distal end of the implant, and when its distal end is in its inserted state in the sheath, the implant is separable from its gripper by moving the sheath and the gripper relative to each other in the direction that breaks the alignment between the sheath and the gripper, until the implant passes through the slot of the gripper, said sheath being provided with a bearing seat against which the implant bears both when said implant is in its inserted state in the sheath, and when said implant is in its state separated from its gripper.

As a result of the sheath co-operating with the gripper to form a grip zone so as to make it easier to remove the implant from the gripper without touching the implant, the gripper may substantially surround the implant during the storage and transport stages, something that is not possible in the prior art, in which the head of the implant must be left accessible.

As a result of the sheath being provided with a seat that forms a seat for the implant, it is possible, by means of a handling tool, to exert axial thrust on the head of the implant so as to couple the implant with the tool by engaging complementary shapes, without causing the implant to move axially within the sheath.

Naturally, at least at its seat, the "rigid" sheath is made of a material that presents elasticity that is less than the elasticity of the body of the gripper, so as to limit deformation of the sheath.

Preferably, said kit further comprises a storage element for storing the implant prior to its separation from the gripper, said storage element including at least one reception location that is suitable for housing, by interfitting at least in part, firstly at least the distal end of the body of the gripper, and secondly the distal portion of the implant that projects from the gripper.

As a result of the distal end of the gripper body being interfitted, at least in part, in a reception location of the storage element, the effect of clamping, by constricting the gripper body around the implant, can be reinforced, and the risks of the gripper and implant assembly accidentally leaving a reception location during the stages of storing and transporting the kit are reduced, or even eliminated.

Preferably, the sheath is mounted securely to the storage element.

This results in a simplification of the kit and a reduction in the risk of losing the sheath. Furthermore, when the kit includes a plurality of grippers, each associated with a respective implant, a single sheath may be used for all of the gripper and implant pairs.

Preferably, the storage element is made up of at least one plate that is provided with at least two cavities, at least one of the cavities corresponding to a reception location for receiving a gripper that is pre-fitted with its implant, while at least one of the cavities forms at least a portion of said sheath.

Preferably, the body of the gripper is a stepped tubular body with a shoulder, said "outer peripheral" shoulder, on going from the distal end towards the proximal end of said body, forming an abutment that limits the extent to which the body can be inserted inside a reception location of the storage element.

The portion of the gripper that extends between the proximal end and the shoulder of the gripper thus forms the grip portion of the gripper when the gripper and its associated implant are in their stored state in the storage element, while the gripper portion that extends between the shoulder and the distal end of the gripper is the portion of the gripper that is interfitted, at least in part, in the reception location of the storage element. This portion is thus not directly accessible. Since it is adjacent to the uncovered distal portion of the implant, itself housed in the reception location of the storage element, there is normally no chance of the operator's hand touching the implant when the gripper is taken hold of with a view to removing it from the reception location of the storage element.

Preferably, the axial cavity of the body of the gripper includes a constriction zone for constricting the implant, inside which zone the implant is suitable for being held by being clamped.

Preferably, when the implant is in its inserted state in the cavity of the gripper, the head of the implant is at a distance from the proximal end of the gripper.

Once again, this arrangement limits the risks of the surgeon's hand touching the implant.

Preferably, when the gripper is in its unstressed state, the longitudinal edges of the slot of the gripper are spaced apart by a distance that is less than 1 millimeter (mm), so as to avoid the surgeon's hand coming into contact with the implant through the slot.

Preferably, the kit further comprises identification means for identifying the implant that is sandwiched between a portion of the gripper and the storage element, when the implant and its associated gripper are in their inserted state in a reception location of the storage element.

This arrangement enables an operator to access the identification means without the identification means being previously handled by the medical personnel involved in the operation of implanting the implant, such as the surgeon.

The invention also provides a method of preparing to implant an implant of a kit as described above, said implant and the gripper of said kit being associated with each other beforehand;

said method being characterized in that it comprises at least a step of manually taking hold of the gripper associated with its implant, and of inserting the implant in said sheath via its distal end, a step of separating the implant from its gripper by moving the sheath and the gripper relative to each other in the direction that breaks the alignment between the sheath and the gripper, until the implant passes through the slot of the gripper, and a step of holding the implant in the sheath by pressing against a seat of said sheath until the implant is taken hold of by a handling tool that can be coupled, preferably by force, with the head of said implant.

In a particular implementation of the method in which the implant and its associated gripper are previously stored in the storage element of said kit, said method includes, during the step of manually taking hold of the gripper, a stage of removing the gripper and its associated implant from the reception location of the storage element.

The invention can be well understood on reading the following description of embodiment examples, given with reference to the accompanying drawings, in which:

FIGS. 8 to 10 are perspective views showing the various steps of handling a variant of a kit of the invention;

FIG. 11 is a perspective view showing the sheath in FIGS. 8 to 10 in its stored position in the storage element.

Figure 1:
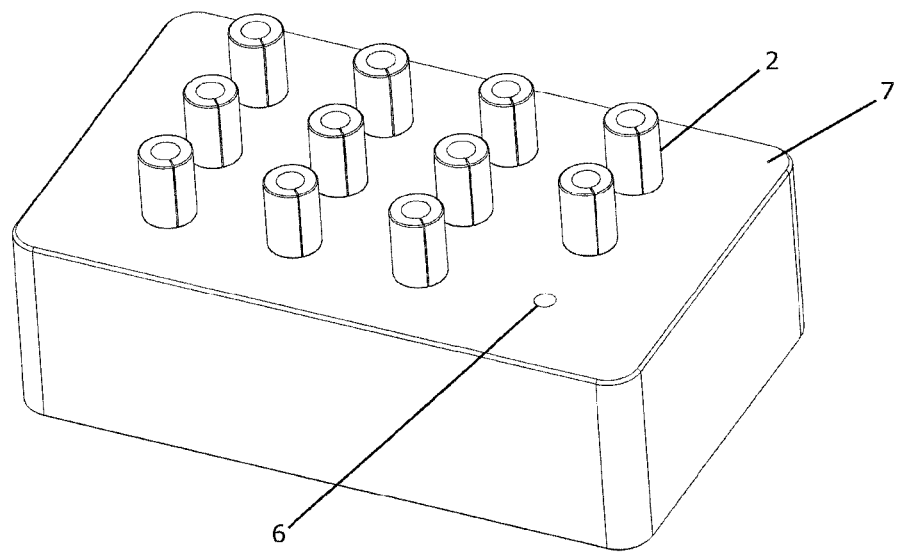
FIGS. 1 to 6 are perspective views showing the various steps of handling a kit of the invention.
Figure 2:
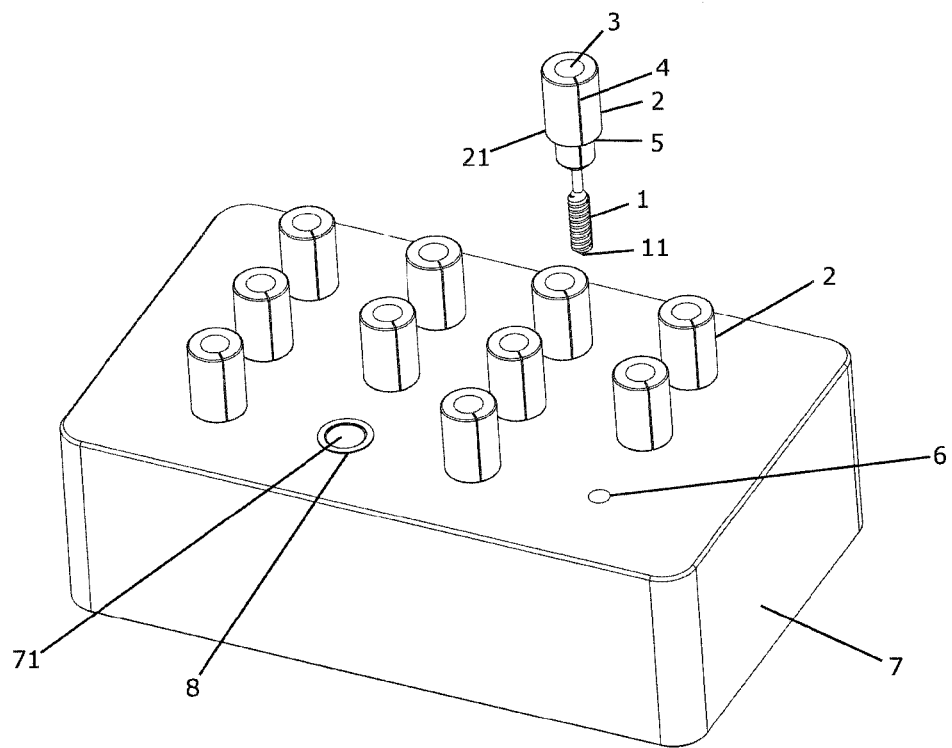
Figure 3:
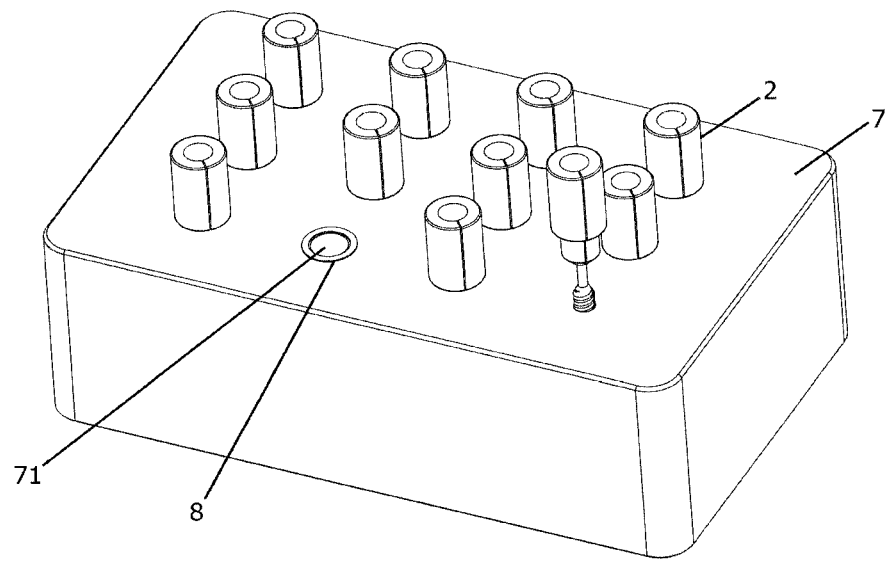

As mentioned above, the kit of the invention is for enabling an implant to be handled safely with a view to implanting said implant in the human or animal body, while limiting any touching of the implant by a hand of the medical personnel involved throughout its handling.

In this embodiment, the kit includes an implant 1 that is in the form of a screw, such as an osteosynthesis screw. The implant 1 comprises a distal end 11 for inserting the implant in the human or animal body, and a proximal end 12, also referred to as the head of the implant, that is suitable for co-operating with a handling tool 9.

To this end, the screw head is provided with a socket that is suitable for coupling, by interfitting complementary shapes, with the end of the handling tool 9 that, in this embodiment, is in the form of a screwdriver.

The kit also includes a gripper 2. In this embodiment, the gripper 2 is in the form of a tubular body 21 of sleeve or bushing type, that is open at each of its ends, and that is slotted longitudinally along its entire length. The body 21 is made of elastomer.

The body 21 has a shoulder. The shoulder 5 is an outer peripheral shoulder going from the distal end towards the proximal end of said body 21. The shoulder 5 forms an abutment that limits the extent to which the body 21 can be inserted inside a reception location 71 of a storage element 7 that is described below.

Figure 7:
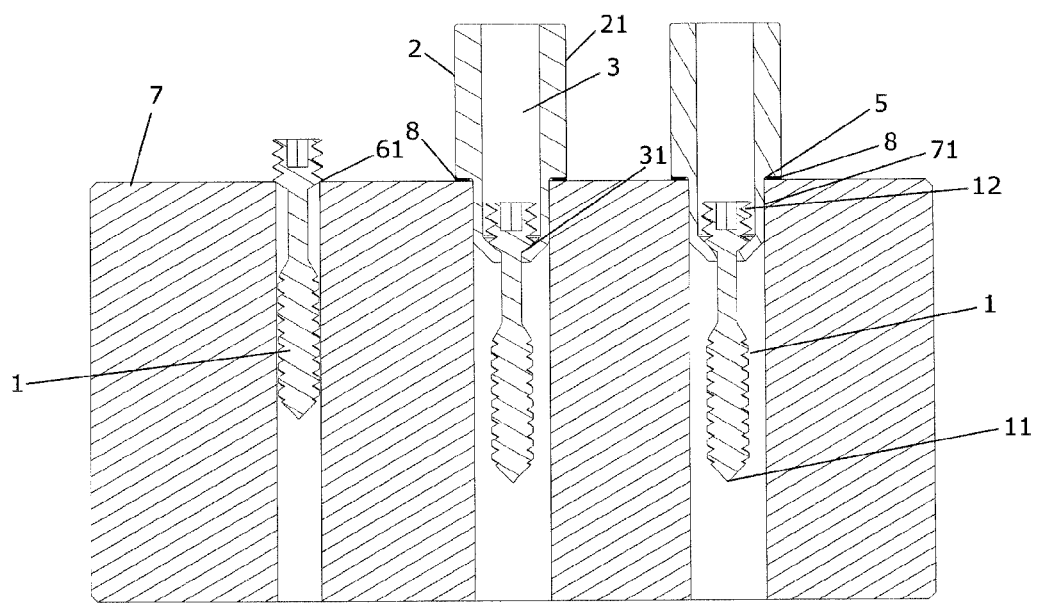
FIG. 7 is a section view showing the storage element taken at a zone of the storage element that includes three cavities, two of the cavities each corresponding to a storage location for storing a gripper and its implant, the third cavity corresponding to a reception sheath for receiving the implant.

The implant is arranged axially inside the axial cavity 3 of the gripper body 21. The distal end 11 of the implant projects from the distal end of the body 21, as shown in FIG. 7, and, when the implant 1 is in its inserted state in the cavity 3 of the gripper 2, the head 12 of the implant is at a distance from the proximal end of the gripper 2.

In particular when the gripper is in its stored state in a storage element that is described below, the grip portion of the gripper is thus formed by the portion of the gripper that extends between the proximal end and the shoulder 5 of the gripper 2.

The axial cavity 3 of the body 21 of the gripper also includes a constriction zone 31 for constricting the implant 1, inside which zone the implant is suitable for being held by being clamped. In this embodiment, the constriction zone is formed by constricting the distal end of the gripper body. When the implant is in its inserted state in the gripper, the constriction extends immediately below the head of the implant into the connection zone for connecting the head of the implant to the body of the implant, as shown also in FIG. 7.

The kit also includes means for assisting in separating the gripper 2 from the implant, and a storage element 7 for storing the implant prior to separating it from the gripper 2.

The storage element 7 includes at least one reception location 71 that is suitable for housing firstly at least the distal end of the body 21 of the gripper 2 by interfitting therewith at least in part, and secondly the distal portion of the implant 1 that projects from the gripper.

In the embodiments shown, the storage element 7 is made up of a thick plate that may constitute the body of a box that is closed by a cover, or it may be inserted inside an instrumentation box that is closed by a cover. This cover, which is not shown, comes to cover the top face of the plate.

The top face of the plate is provided with a plurality of cavities, specifically twelve cavities in this embodiment. Eleven of the cavities each correspond to a reception location 71 for receiving a gripper 2 that has been pre-fitted with its implant 1. Each time, the implant and the gripper are arranged so that the grip portion of the gripper projects from the top surface of the plate, while the portion of the gripper that extends between the shoulder and the distal end of the gripper is interfitted in the cavity.

The portion of the implant projecting from the gripper, that in this embodiment corresponds to the screw body, is also housed in the cavity, as is the head of the screw that is held in the gripper by the constriction zone of the gripper.

In this embodiment, the twelfth cavity of the storage element forms all or part of the means for assisting in separating the gripper from the implant. Specifically, the means for assisting in separating the gripper comprise at least one sheath 6 for receiving the distal end 11 of the implant.

The sheath 6 includes a bearing seat 61 against which the implant 1 bears both when said implant 1 is in its inserted state in the sheath 6, and when said implant 1 is in its state separated from its gripper. Separation takes place as follows:

When the distal end of the implant 1 is in its inserted state in the sheath 6, the implant is separated from the gripper by moving the sheath 6 and the gripper 2 relative to each other in the direction that breaks the alignment between the sheath 6 and the gripper 2, until the implant 1 passes through the slot 4 of the gripper 2.

Figure 4:
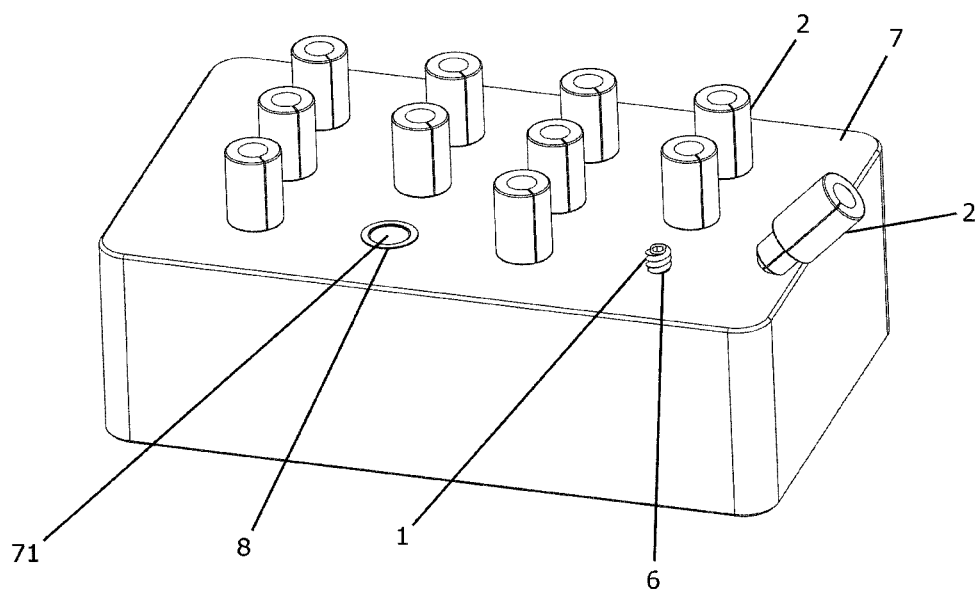

Such relative movement may result in the gripper tilting or pivoting relative to the sheath, in particular relative to the longitudinal axis of the sheath, as shown in FIGS. 4 and 10. Such tilting may take place by moving the proximal end of the gripper away from the longitudinal axis of the sheath, as shown in the figures, or by moving the distal end of the gripper away from the longitudinal axis of the sheath, for example.

Figure 12:
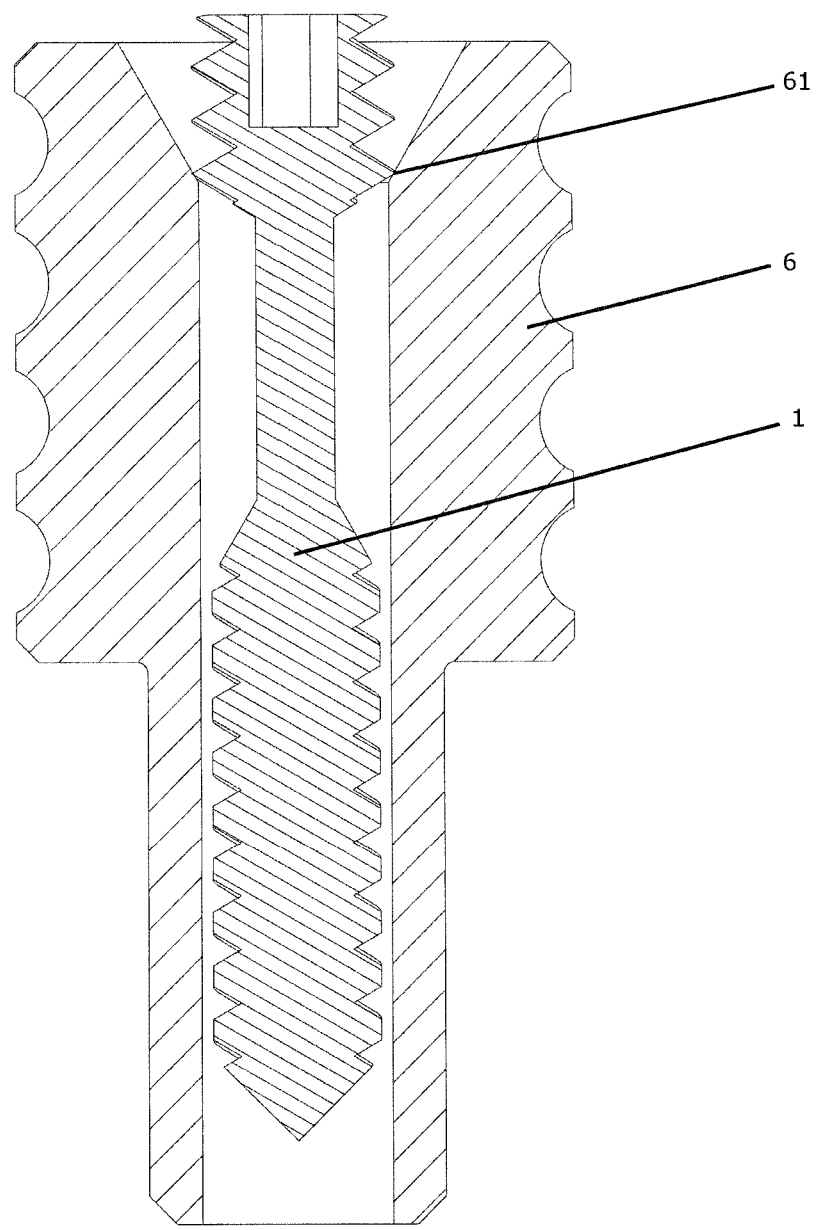
FIG. 12 is a section view showing the FIG. 11 sheath, with an implant in its inserted state in said sheath.

Once the gripper has been eliminated, the implant remains in the sheath, bearing against the seat of said sheath, as shown in FIGS. 7 and 12, for example. The seat that forms a seat for the implant, in particular for the head of the implant in this embodiment, may be formed by the end of the sheath via which the implant is inserted into the sheath (FIG. 7), or by a constriction or a narrowing in the passage defined by said sheath (FIG. 12).

The seat formed in this way enables the implant to bear against this seat when its proximal end is subjected to axial thrust resulting from the operation of coupling the implant with the handling tool 9. Generally, the seat of the sheath is configured to hold the head of the implant in a position close to an open end of the sheath, so as to facilitate co-operation between the implant and the handling tool.

It should be observed that the sheath may equally well be a blind sheath or a through sheath. In addition, the sheath may be mounted in non-removable manner on the storage element, as shown in FIGS. 1 to 4, in which the sheath is formed merely by a cavity in the storage element.

Alternatively, the sheath may be formed by a tubular part that can be inserted, in part, into a cavity in the storage element, as shown in FIGS. 10 and 11. In this configuration, the sheath can be coupled to the storage element in removable manner. At least one of the cavities in the storage element thus forms a reception space for receiving the sheath.

Finally, in an embodiment that is not shown, the sheath may be entirely independent of the storage element.

The kit may also include identification means 8 for identifying the implant 1, which identification means are sandwiched between a portion of the gripper 2 and the storage element 7, when the implant 1 and its associated gripper 2 are in their inserted state in a reception location 71 of the storage element 7.

In this embodiment, the identification means 8 are in the form of a washer that is positioned around a reception location of the storage element. The washer carries a marking that can be read once the implant and its gripper are removed from the storage element.

During storage and transport stages, the washer is held between the top face of the plate constituting the storage element and the stepped surface of the gripper.

The washer generally presents thickness of about 0.2 mm. The washer presents an inside diameter that is greater than the diameter of the cavity that it surrounds in the storage element, and that is greater than the diameter of the gripper portion that it surrounds, and preferably less than the diameter of the grip portion of the gripper.

Figure 5:
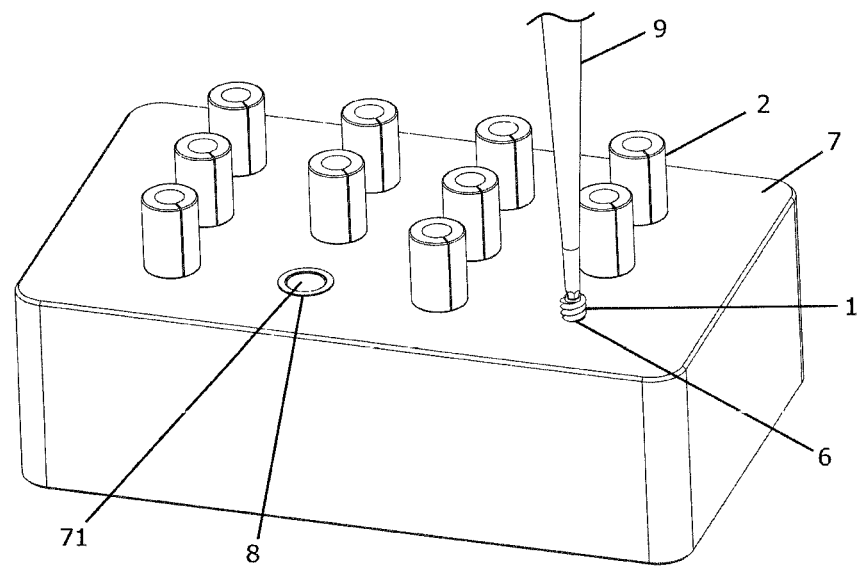
Figure 6:
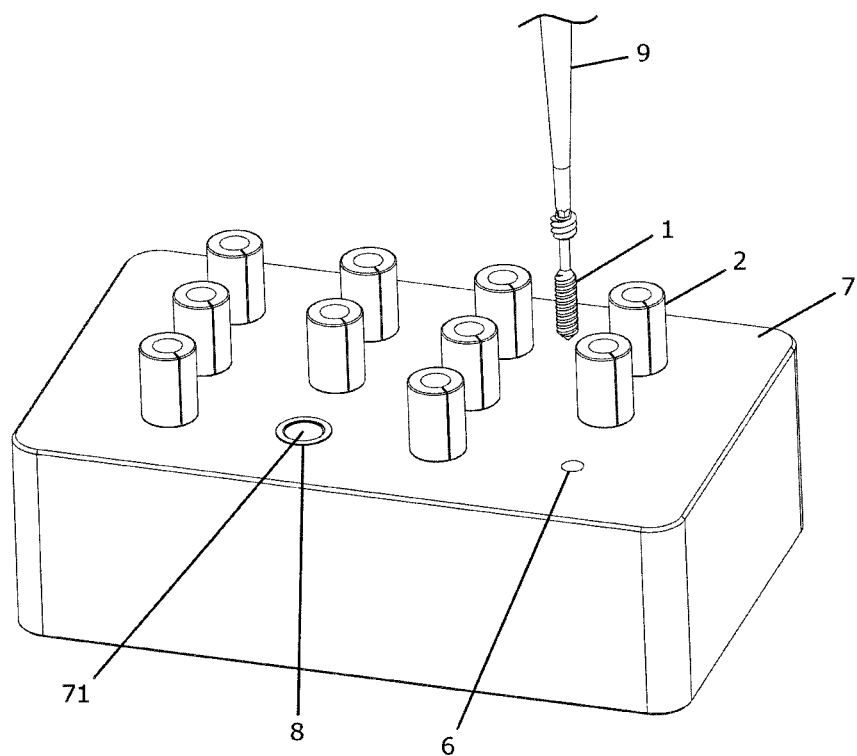

In practice, an implant of a kit as described above is prepared and implanted as follows:

With the implant stored with its gripper in a storage element, as shown in FIG. 1, the operator, such as a surgeon, initially takes hold of the gripper by its grip portion so as to remove the implant and the gripper from the storage element (FIG. 2), then positions the distal end of the implant in the sheath (FIG. 3) before separating the gripper from the implant by tilting the gripper (FIG. 4). The screwdriver is inserted into the head of the implant (FIG. 5), and the screw, manipulated by means of the screwdriver coupled to the screw, is removed from the sheath (FIG. 6). The screw is then ready to be implanted in a body.

It should be observed that the operator has no need at any time to touch the implant directly.

The invention claimed is:

1. A kit comprising at least:
an implant that presents a distal end for inserting the implant into the human or animal body, and a head of the implant, that is suitable for co-operating with a handling tool;
a gripper for gripping said implant, the gripper being in the form of a hollow elongate body that is open at at least one end, and that is slotted longitudinally along its entire length, the body being made, at least in part, of an elastically-deformable material that tends to return the edges of the slot towards each other, the slot of said body opening out into an axial cavity of said body, inside which the implant is insertable, with said distal end of said implant projecting from a distal end of said body;
said kit further comprising means for assisting in separating the gripper from the implant without touching the implant, the means comprising at least one reception sheath for receiving the distal end of the implant, and when its distal end is in its inserted state in the sheath, the implant is separable from its gripper by moving the sheath and the gripper relative to each other in the direction that breaks the alignment between the sheath and the gripper, until the implant passes through the slot of the gripper, said sheath being provided with a bearing seat against which the implant bears both when said implant is in its inserted state in the sheath, and when said implant is in its state separated from its gripper.

2. A kit according to claim 1, further comprising a storage element for storing the implant prior to its separation from the gripper, said storage element including at least one reception location that is suitable for housing, by interfitting at least in part, firstly at least the distal end of the body of the gripper, and secondly the distal portion of the implant that projects from the gripper.

3. A kit according to claim 2, wherein the sheath is mounted securely to the storage element.

4. A kit according to claim 2, wherein the storage element is made up of at least one plate that is provided with at least two cavities, at least one of the cavities corresponding to a reception location for receiving a gripper that is pre-fitted with its implant.

5. A kit according to claim 4, wherein at least one of the cavities forms at least a portion of said sheath.

6. A kit according to claim 2, wherein the body of the gripper is a stepped tubular body with an outer peripheral shoulder, said outer peripheral shoulder, going from the distal end towards the proximal end of said body, forming an abutment that limits the extent to which the body can be inserted inside a reception location of the storage element.

7. A kit according to claim 1, wherein the axial cavity of the body of the gripper includes a constriction zone for constricting the implant, inside which zone the implant is suitable for being held by being clamped.

8. A kit according to claim 1, wherein when the implant is in its inserted state in the cavity of the gripper, the head of the implant is at a distance from the proximal end of the gripper.

9. A kit according to claim 2, further comprising identification means for identifying the implant that is sandwiched between a portion of the gripper and the storage element, when the implant and its associated gripper are in their inserted state in a reception location of the storage element.

\* \* \* \* \*